US009302831B2

(12) United States Patent
Wilson et al.

(10) Patent No.: US 9,302,831 B2
(45) Date of Patent: Apr. 5, 2016

(54) REAGENT BOTTLES, VALVES THEREFOR, WASHING MODULES AND METHODS AND APPARATUS FOR DISPENSING REAGENTS

(75) Inventors: Gareth Wilson, Waringstown (GB); Carl Wrigglesworth, Bristol (GB); Peter Fitzgerald, Crumlin (GB); John Lamont, Crumlin (GB); Ivan McConnell, Crumlin (GB)

(73) Assignee: Randox Laboratories Ltd., Crumlin (GB)

( * ) Notice: Subject to any disclaimer, the term of this patent is extended or adjusted under 35 U.S.C. 154(b) by 184 days.

(21) Appl. No.: 13/812,691

(22) PCT Filed: Jul. 26, 2011

(86) PCT No.: PCT/GB2011/051425
§ 371 (c)(1),
(2), (4) Date: Jan. 28, 2013

(87) PCT Pub. No.: WO2012/013970
PCT Pub. Date: Feb. 2, 2012

(65) Prior Publication Data
US 2013/0121878 A1    May 16, 2013

(30) Foreign Application Priority Data

Jul. 26, 2010 (GB) .................................. 1012494.9

(51) Int. Cl.
| A61B 10/00 | (2006.01) |
| B65D 51/24 | (2006.01) |
| B01L 3/00 | (2006.01) |
| B65D 51/00 | (2006.01) |
| G01N 35/10 | (2006.01) |
| G01N 35/04 | (2006.01) |

(52) U.S. Cl.
CPC .............. B65D 51/243 (2013.01); B01L 3/523 (2013.01); B65D 51/002 (2013.01); G01N 35/1002 (2013.01); *B01L 2300/044* (2013.01); *G01N 2035/0401* (2013.01)

(58) Field of Classification Search
CPC ...................... B01L 2300/044; G01N 35/1002
See application file for complete search history.

(56) References Cited

U.S. PATENT DOCUMENTS

| 6,050,435 A | 4/2000 | Bush et al. |
| 6,054,099 A * | 4/2000 | Levy ............................. 422/547 |
| 6,361,744 B1 * | 3/2002 | Levy ............................. 422/570 |
| 6,375,021 B1 | 4/2002 | Slenker |
| 6,716,396 B1 | 4/2004 | Anderson et al. |
| 2006/0088446 A1 | 4/2006 | Heck et al. |
| 2009/0325309 A1 | 12/2009 | Favuzzi et al. |

OTHER PUBLICATIONS

Oct. 6, 2011 International Search Report issued in International Patent Application No. PCT/GB2011/051425.
Oct. 6, 2011 Written Opinion of the International Searching Authority issued in International Patent Application No. PCT/GB2011/051425.

* cited by examiner

*Primary Examiner* — Jyoti Nagpaul
(74) *Attorney, Agent, or Firm* — Oliff PLC

(57) ABSTRACT

A valve for a reagent bottle is provided, the valve including a resilient membrane configured to extend across an opening in the reagent bottle, the resilient membrane having at least one slit extending therethrough. Also disclosed is a dispensing apparatus for dispensing a reagent from a reagent bottle, the dispensing apparatus comprising: a probe assembly having a probe adapted for insertion into the reagent bottle through the valve and an extraction mechanism for drawing reagent out of the reagent bottle through the probe. A valve opening assembly is provided, which is adapted to open the valve of the reagent bottle such that the probe can pass through the valve without contacting the valve.

14 Claims, 8 Drawing Sheets

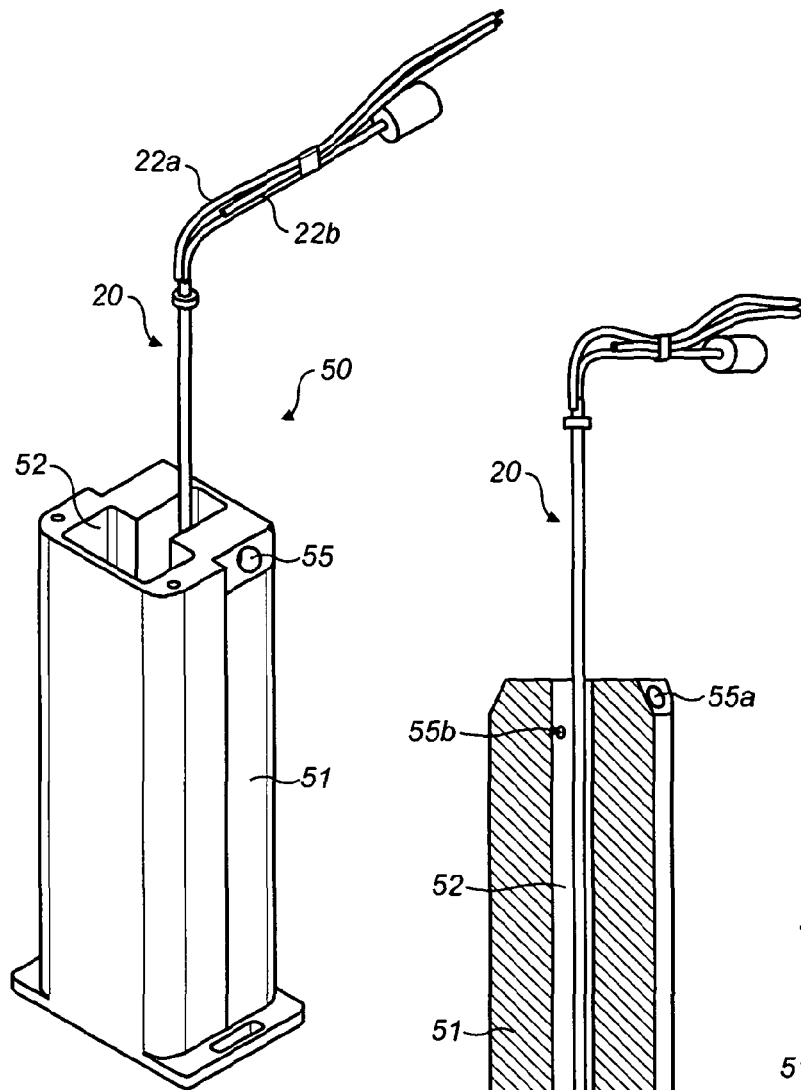
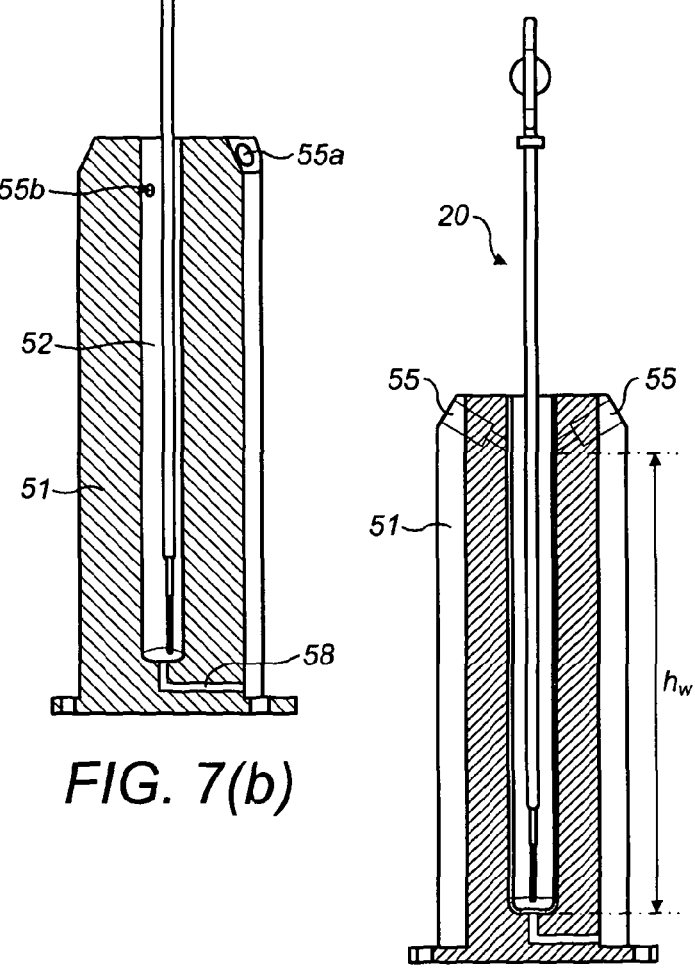
FIG. 7(a)
FIG. 7(b)
FIG. 7(c)

REAGENT BOTTLES, VALVES THEREFOR, WASHING MODULES AND METHODS AND APPARATUS FOR DISPENSING REAGENTS

This invention relates to valves for reagent bottles, reagent bottles, washing modules and techniques for dispensing reagents, all for use in analysers such as diagnostic analysing systems.

Automated diagnostic analysers use chemical reagents to perform tests on various types of samples. Once a reagent bottle is opened the contents are exposed to air. This gradually degrades the reagent and limits the length of time it can be used once open—this is referred to as "Open Stability". Reagents are reactive chemicals which, compared with inert substances such as water and other diluents, have a very short shelf life. For instance, typical reactants can only be exposed to air for a matter of days before they must be disposed of. It is desirable to extend the lifetime of the reagents in order to minimise wastage and reduce the frequency of replenishing.

Conventional reagent bottle closures have included lids such as screw-on caps or clip-on lids which are usually manually engaged with the bottle and manually removed at time of use. As a result, the bottles are typically left open for the duration of a series of tests, e.g. many hours or even days. Automated systems for the removal and replacement of such lids are feasible but mechanically complex and prone to breakdowns. Some alternative arrangements have been proposed such as that disclosed in U.S. Pat. No. 6,375,021, in which a self-closing bottle cap is formed with a hinge-mounted cover plate. The cover plate is easily pushed aside upon contact with a swab stick, and pivots aside and upward allowing the swab stick to enter the bottle. Upon removal, the cover plate returns to its original position under the action of gravity. Whilst such arrangements provide some benefit, however, the degree of sealing achieved is often not high and, moreover, the complex mechanical construction of the closure is expensive and prone to breakage.

Presently disclosed is a system for extending the viable life of a diagnostic reagent by minimising its interaction with atmosphere. Whilst the following description focuses on an automated system, the methodology could equally well be applied to a manual aspiration (or other dispensing) system.

According to a first aspect of the present invention, a valve for a reagent bottle is provided, the valve comprising a resilient membrane configured to extend across an opening in the reagent bottle, the resilient membrane having at least one slit extending therethrough.

Thus, a key concept of the system is to limit the exposure of the reagent to the air by minimising air circulation into and out of the reagent bottle. This can be done for example using a self-sealing valve, e.g. a silicone or rubber cross-slit valve, at the neck of the bottle that can be opened by means of a probe or sleeve pushing through the valve. Once the probe is removed the valve self-closes again to reseal the bottle, thereby excluding the atmosphere and extending the shelf-life of the reactant. A "slit" is a cut through the membrane, the edges of which preferably wholly contact one another when the membrane is not under stress, so as to form a atmospheric seal. "Slits" can be straight or curved or both.

By forming the closure from a resilient material in this way, a highly effective seal can be achieved. The construction requires no moving parts and is thus robust and inexpensive. Further, since the seal opens only to the extent required to accommodate the passage of the probe or sleeve therethrough, the degree of exposure of the reactant to the environment is kept to a minimum not only before and after the dispensing procedure, but also during.

Preferably, the membrane is adapted to undergo a reversible deformation in order to accommodate the passage of a probe through the at least one slit, and to revert to a sealed configuration in which the slit is substantially closed upon removal of the probe, whereby the valve is self-sealing. In the closed position, the edges of the slits should preferably meet one another along their full length, such that no opening remains. This ensures that the seal acts as an atmospheric barrier, excluding air and humidity from the bottle interior. In preferred examples, the membrane has at least two slits extending through the membrane, the at least two slits intersecting one another preferably at a single position. Advantageously, the angle between angularly adjacent pairs of the at least two slits is substantially equal, preferably approximately 90 degrees. In a desirable implementation, the at least two slits are arranged to form a cross-slit.

The resilient membrane could be formed of any suitable material but preferably comprises a plastics material, preferably rubber or a silicone-based polymer. Silicone is most preferred since the material is both inert and resistant to a wide variety of reagents, and also possesses high resilience leading to reliable self-closing of the valve.

To ensure a tight seal, the at least one slit is preferably a post-moulded cut. That is, the valve is formed in two steps, cutting the slit through the membrane after it has been moulded into shape. Preferably a blade is used to carry out the cutting such that no material is removed. This should be contrasted for example with slits made at the time of moulding a membrane, in which case there will inevitably be regions in which the two edges of each slit do not contact one another when the valve is in the closed position.

Hence the invention further provides a method of manufacturing a valve as described above, comprising moulding the resilient membrane and then forming the at least one slit by cutting through the resilient membrane with substantially no removal of material.

Valves of the sort described above have not previously been used in the field of reactant bottles, which are commonly closed using a lid such as a screw top in order to achieve the necessary atmospheric seal. The lid must be removed prior to use of the bottle and replaced afterwards. This not only requires additional user input and handling of potentially hazardous substances, but also leaves the bottle uncovered during the period of use. Hence the present invention contemplates the use of a valve as described above for closing a reagent bottle in a medical device, preferably an analyser for performing medical, chemical, proteomic, molecular and/or biochemical tests.

In another aspect of the invention, a reagent bottle for use in an analyser is provided, comprising a valve as described above. Preferably, the periphery of the resilient membrane is affixed to the reagent bottle around the edge of an aperture provided in the reagent bottle. In preferred examples, the valve is joined to the reagent bottle by over-moulding the reagent bottle with the flexible membrane such that the valve is integrated into the reagent bottle. Alternatively, the valve can be housed in an insert member fitted to the reagent bottle, the resilient membrane being affixed to the insert member. Preferably, the insert member is fitted to the reagent bottle inside a neck portion of the reagent bottle. The insert member may comprise a lid or cap fitted to the reagent bottle. Any suitable joining technique could be used—e.g. the insert member could be fitted to the reagent bottle by heat sealing, ultrasonic welding, an adhesive, or a mechanical fixture such as a snap fit or threaded screw fit. Similarly, the resilient membrane is preferably affixed to the reagent bottle or insert member by adhesive, ultrasonic welding, heat sealing or a mechanical fixture such as a clamp or press fit.

According to another aspect of the invention, a dispensing apparatus for dispensing a reagent from a reagent bottle as described above is provided, the dispensing apparatus comprising: a probe assembly having a probe adapted for insertion into the reagent bottle through the valve and an extraction mechanism for drawing reagent out of the reagent bottle through the probe.

An added consideration with analysers is the carryover between different samples and reagents which can give inaccurate or incorrect readings. The use of a valve as described above can lead to the probe becoming contaminated with reagent on its surface at positions away from the probe tip: this is because reagent may be deposited on the valve membrane as a probe passes therethrough, and this may coat the sides of the probe as it is inserted or removed. Typical probe washing stations are configured only to clean the tip region of a probe: this is necessary in order to wash the probe sufficiently fast to maintain high throughput. To address this problem, in a preferred implementation, the dispensing apparatus therefore further comprises a valve opening assembly adapted to open the valve of the reagent bottle such that the probe can pass through the valve without contacting the valve. In this way, only the tip region of the probe will contact the reagent and can be washed in the usual way. For example, a method of eliminating the carryover effect now proposed involves opening the valve using a separately actuated sleeve and then passing the probe (e.g. an automated syringe) through this sleeve, isolating it from the valve and any residue on it. Hence, advantageously, the valve opening assembly comprises a sleeve and an actuator for abutting the sleeve against the resilient membrane of the valve so as to deform the membrane and thereby open the at least one slit such that the probe can pass therethrough.

Preferably, the actuator is adapted to insert the sleeve through the at least one slit such that the sleeve isolates the valve from the sleeve interior through which the probe can pass. Advantageously, the sleeve comprises a hollow tube of any cross-section such as circular or square. The tube need not have a complete circumference—e.g. the cross section could be "C" or "U" shaped. Any sufficiently rigid material could be used for the sleeve. In particular examples, the sleeve is formed of a metal or plastics material, preferably a corrosion resistant metal, a protectively coated metal or an inert polymer.

In certain preferred embodiments, the valve opening assembly further comprises a washing mechanism for washing the sleeve. For example, this may take the form of a washing station to which the sleeve can be moved when washing is required. The washing station could be provided in place of one or more reagent bottles on a reagent carousel, if supplied, or the sleeve could be moveable along a further axis towards a separate wash station.

Advantageously, the sleeve diameter is sufficiently large relative to the valve such that only the outer surface of the membrane is contacted by the sleeve. The sleeve and actuator should preferably be configured such that the sleeve does not contact any reagent inside the reagent bottle.

The dispensing apparatus preferably further comprises a probe drive mechanism for at least driving the probe into and out of the reagent bottle. A controller may be provided for controlling the extraction mechanism and/or the valve opening assembly and/or the probe drive mechanism.

Preferably, the apparatus is adapted to accommodate a plurality of reagent bottles wherein the probe assembly is movable relative to the plurality of reagent bottles such that the probe can extract reagent from each or at least some of the plurality of reagent bottles. For example, the bottles could be arranged on a carousel which is rotatable for interaction with the probe at a predetermined position. Alternatively, the probe could be movable between the different bottles.

Similarly, the valve opening assembly is preferably moveable relative to the plurality of reagent bottles such that it can open the valves of each or at least some of the bottles. In this way, a single valve opening assembly need be provided. Alternatively, a valve opening assembly could be provided for each reagent bottle.

In another aspect, the present invention provides a washing module for washing a probe used to extract reagent from a reagent bottle, the washing module being adapted to wash substantially the whole length of the probe. This is an alternative way of addressing the problem of cross contamination caused by the aforementioned valve, which can be used instead of (or in addition to) a valve opening assembly.

In a preferred implementation, a washing module for washing a probe used to extract reagent from a reagent bottle, comprises a chamber for accommodating the probe, a fluid input device adjacent the top of the chamber and a fluid extraction device adjacent the bottom of the chamber, whereby a flow of fluid through the chamber can be established. Preferably, the fluid input and extraction devices are arranged such that substantially the whole length of the probe is submersed in the flow of fluid. For instance, at least half of the length of the probe may be washed, more preferably at least 75% of the probe. Most advantageously, the washing module is adapted to wash at least a length of the probe corresponding to the height of the reagent bottle(s) from which the probe extracts reagents—i.e. the full section of the probe which is inserted into the regent bottle during reagent dispensation. In particular examples, the fluid input comprises one or more jets for inserting fluid at high pressure, and/or the fluid extraction device comprises a vacuum pump for extracting the fluid.

The invention also provides an analyser for performing chemical and/or biochemical tests comprising at least one reagent bottle as described above, the reagent bottle preferably containing a reagent for use in processes to be performed by the analyser. In general, the function of such analysers is to perform automated or semi-automated analysis of biological samples. For example, the analyser may be configured to perform immunoassays, proteomic or molecular assays.

Also provided is an analyser comprising a dispensing apparatus and/or a washing module, each as described above.

In another aspect of the invention, a method of dispensing reagent(s) is provided, comprising: a) providing one or more reagent bottles each containing a reagent, wherein each reagent bottle has a valve as described above; b) inserting a probe through the valve of one of the reagent bottles; c) extracting reagent from the bottle through the probe; and d) removing the probe from the bottle such that the valve reseals.

Preferably, prior to step b), the valve is opened such that the probe can be inserted into the bottle without contacting the valve. Advantageously, the valve is opened by abutting a sleeve against the resilient membrane so as to open the at least one slit allowing passage of the probe therethrough. Preferably, the sleeve is inserted through the valve and the probe is inserted through the sleeve such that the probe is isolated from the valve by the sleeve. Advantageously, the sleeve does not contact the reagent in the bottle.

The method may also or alternatively involve washing substantially the whole length of the probe before or after performing steps b) to d). Where the valve is opened before insertion of the probe, preferably the method further comprises washing only the tip of the probe before or after performing steps b) to d).

Examples of valves, reagent bottles, washing modules and techniques for dispensing reagents will now be described with reference to the accompanying drawings, in which:—

Figure 4A:
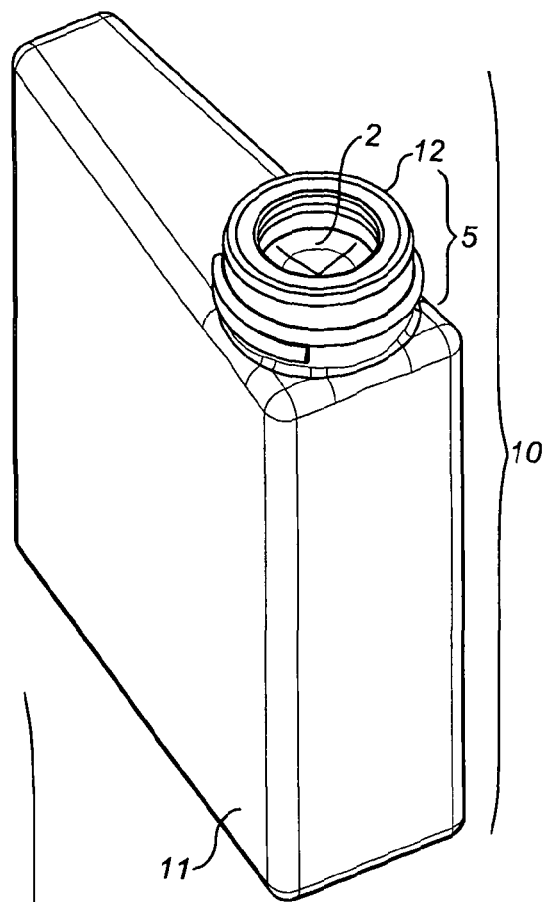
Figure 4B:
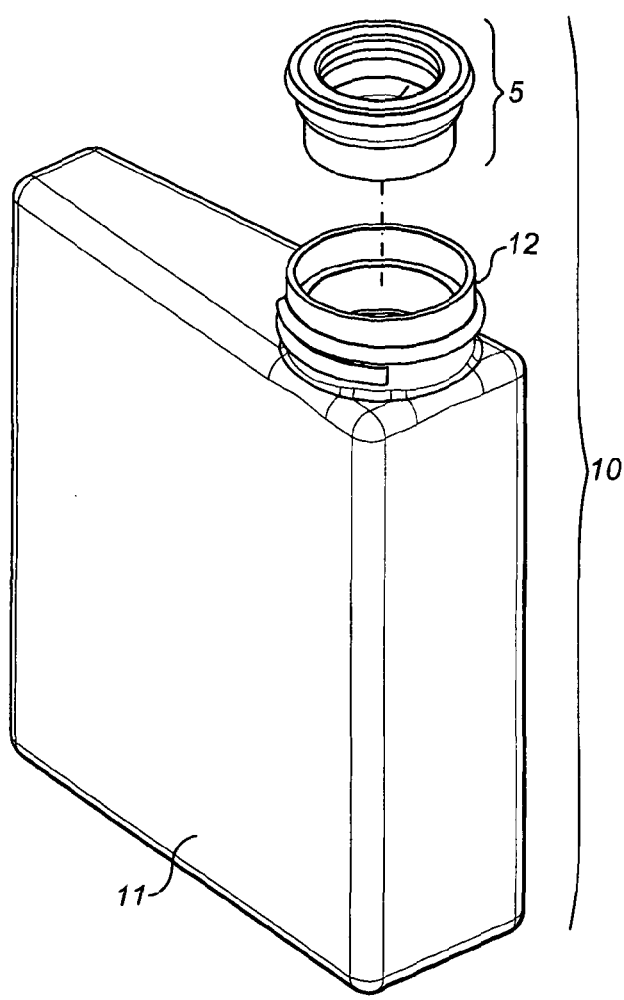
Figure 5:
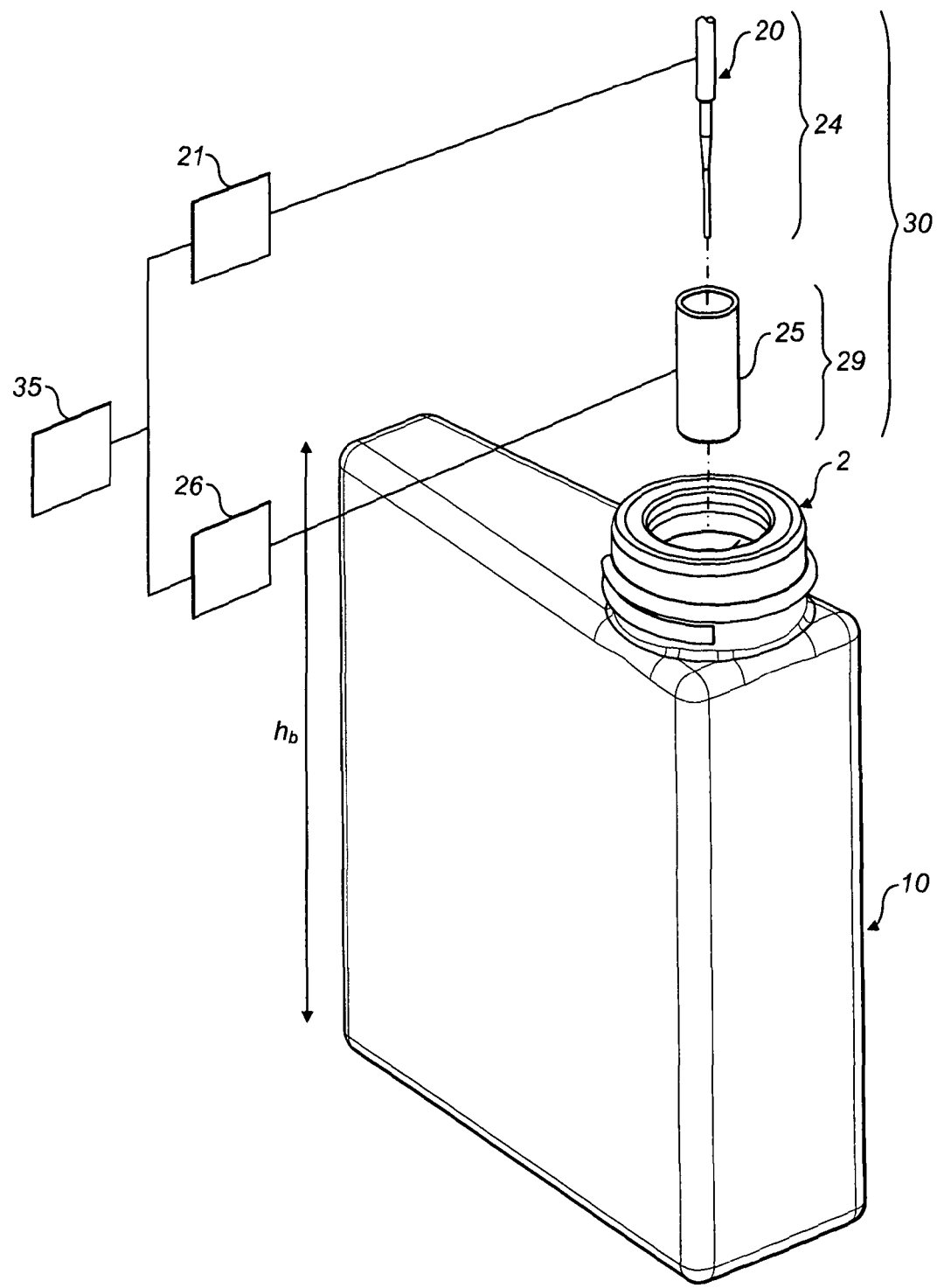
Figure 6:
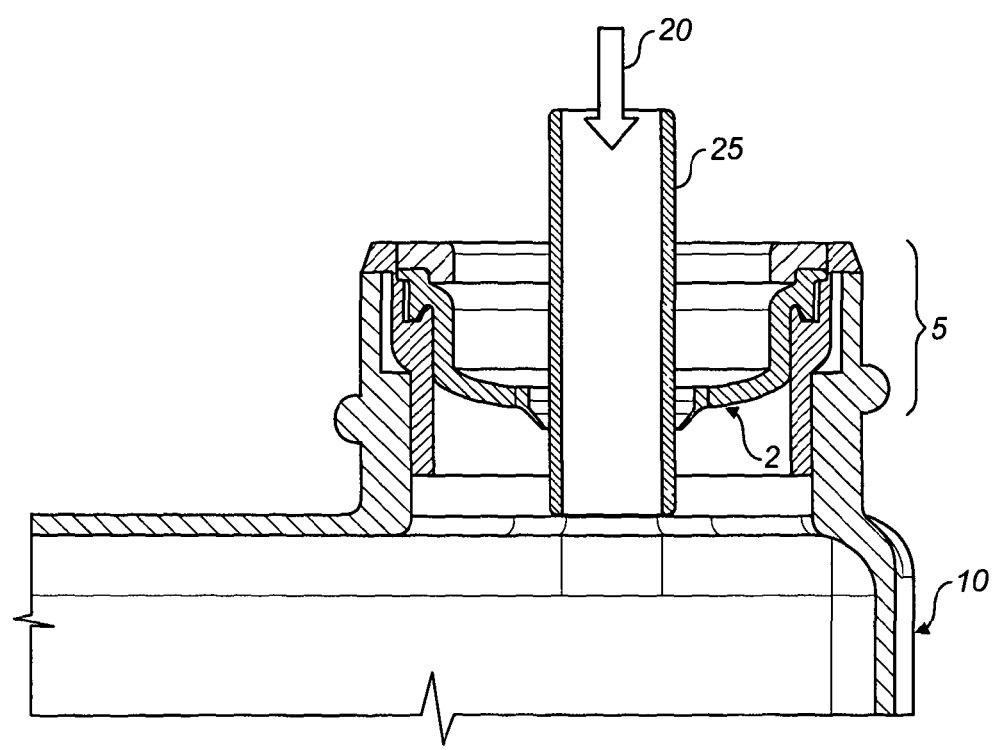
Figure 8A:
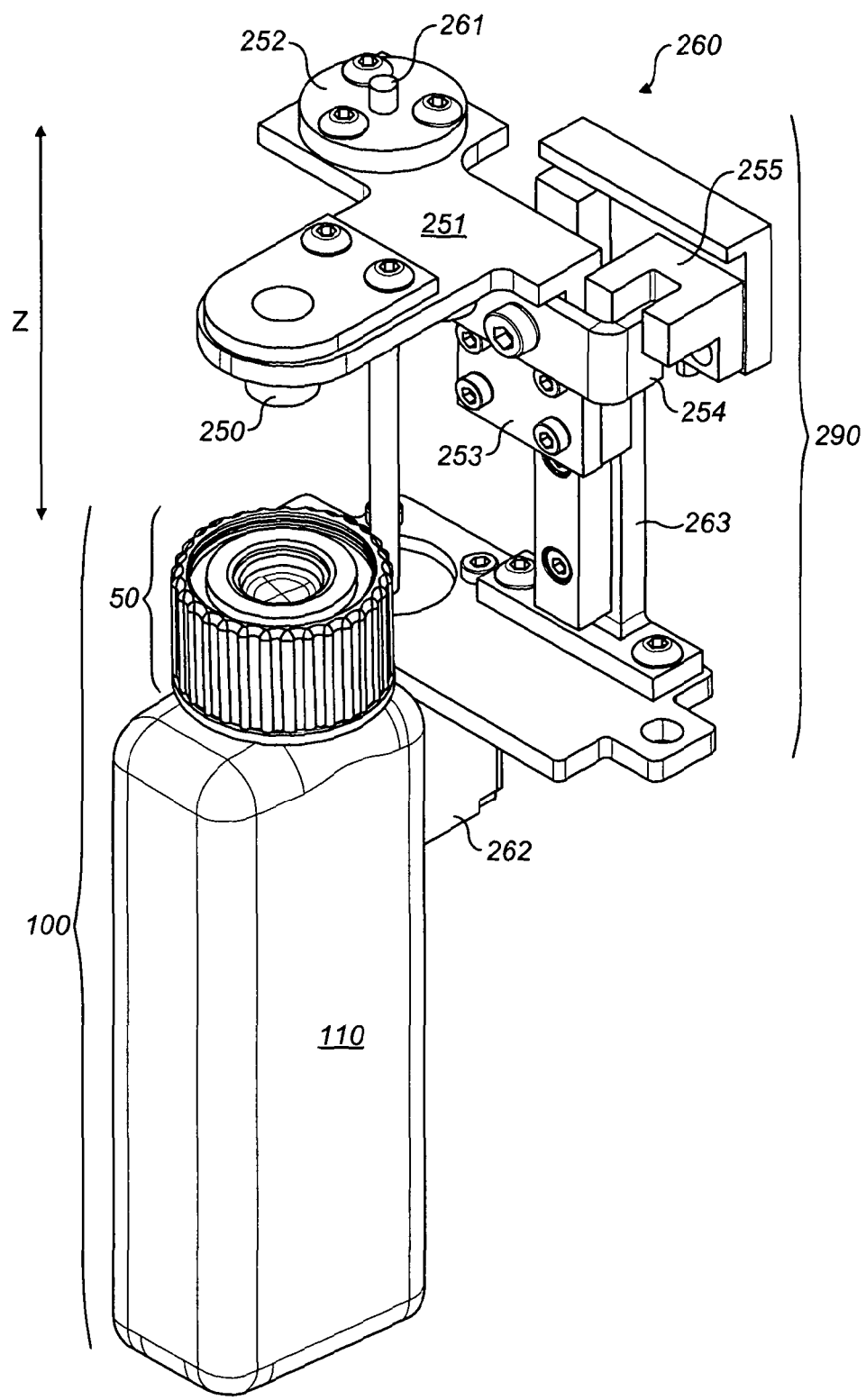
Figure 8B:
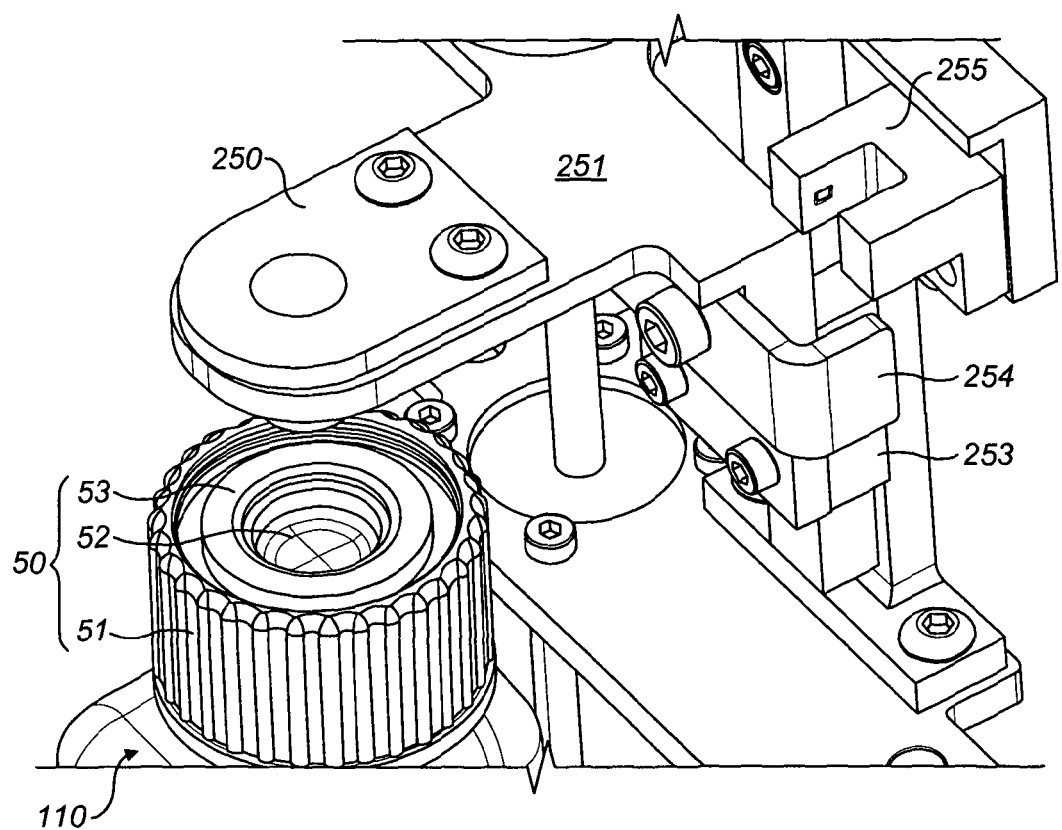
Figure 8C:
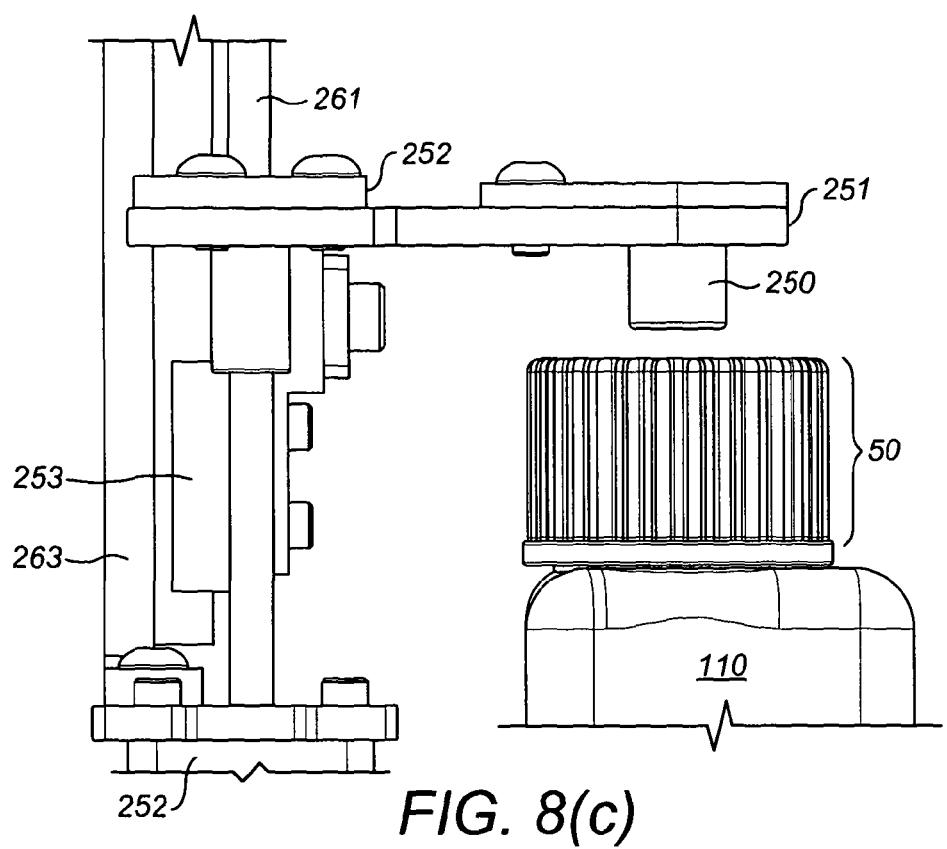
Figure 8D:
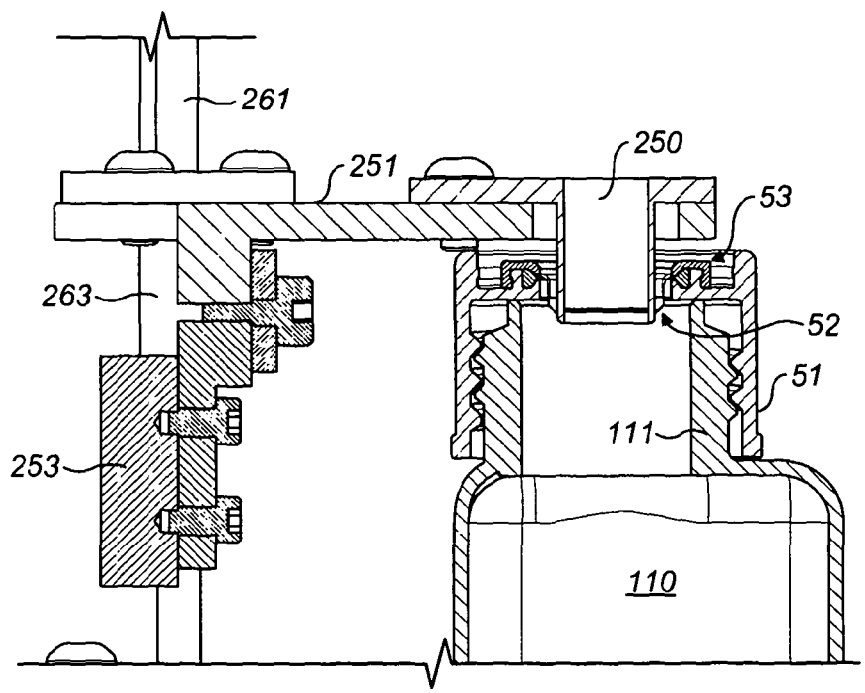

FIGS. 3a to d schematically depict four exemplary valves in plan view;

FIGS. 4a and 4b show an embodiment of a reagent bottle, FIG. 4b showing the valve insert separated from the bottle body;

FIG. 5 depicts selected components of an embodiment of an apparatus for dispensing reagents;

FIG. 6 is a cross section through a portion of the reagent bottle of FIG. 4 during a dispensing step using the apparatus of FIG. 5;

FIGS. 7(a), (b) and (c) show an embodiment of a probe washing module, FIG. 7(a) showing an external perspective view of the module, FIG. 7(b) showing a cut-away perspective view of the module, and FIG. 7(c) showing a cross-section of the module; and FIGS. 8(a) to (d) depict an example of a valve opening assembly in a further embodiment, together with a further embodiment of a reagent bottle.

Components of an exemplary system using the principles of the present invention are described in turn below, alone and in combination with one another. It should be appreciated that any combination of the disclosed components could be utilised.

Valve (or "Seal Insert")

A valve is provided for closing a reagent bottle and limiting contact between the atmosphere and the bottle contents. The valve or seal could be integrated or attached to the bottle in a number of ways including:

Insert moulding—Directly integrated into the reagent bottle by over-moulding;

Clip Insert—The valve is housed in a separate insert which is then inserted into the bottle neck (or other aperture) and held by e.g. snap fit detail or ultrasonic welding;

Cap—the valve could be housed into a separate lid or cap which fits to the bottle by either a snap-fit detail or threaded screw fit.

Figures 1, 2:
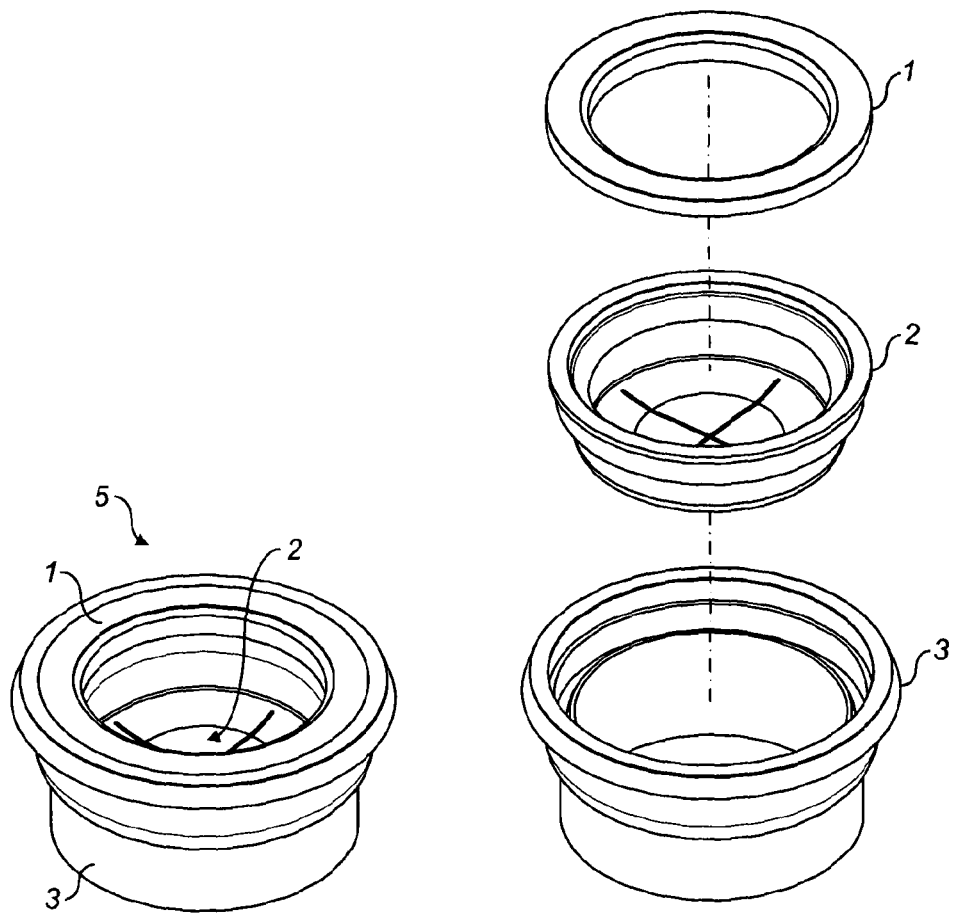
FIG. 1 shows an embodiment of a valve incorporated into an exemplary valve insert for a reagent bottle.
FIG. 2 is an exploded view of the valve insert shown in FIG. 1.

An example of a valve insert 5, comprising a valve 2 mounted into an insert member 3, is shown in FIGS. 1 and 2.

Taking for example the insert method: the valve 2, is held within a valve insert assembly 5, which can be inserted into the neck of a reagent bottle. The valve insert comprises three parts: an insert top or "cap" 1, the valve 2, and a valve seat 3. The valve 2 sits between the insert top 1 and valve seat 3. The top 1 and seat 3 are then joined together, either through press fit, a form of adhesive or ultrasonic welding. This keeps the valve static and allows a probe to pass through the valve.

The valve 2 includes a membrane made for example of rubber or silicone or any other resilient or flexible material, with at least one slit 4 passing therethrough. The slit arrangement through the membrane could take any desirable form such as a single (straight or curved) slit, a cross slit (i.e. two intersecting slits) or multiple slits (e.g. 3 or more) which preferably intersect at a single (central) point. Some examples are shown in FIGS. 3a to d.

In the present example, the valve has a diameter (corresponding to the approximately flat, circular portion of the membrane) of around 10 mm. Each of the two slits (approximately half of each is visible in FIG. 2) has a length of around 8 mm. The membrane has a thickness of around 0.2 mm, although thicker membranes (e.g. 0.3 mm to 1 mm thickness) are also envisaged.

Figures 3A, 3B, 3C, 3D:
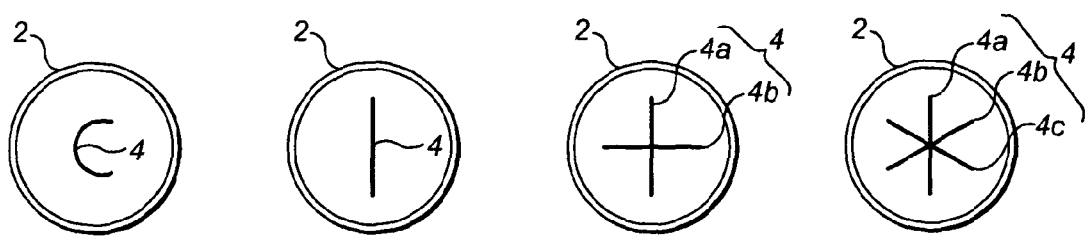

Some alternative slit configurations are shown in FIG. 3. FIG. 3a shows a valve 2 having a single slit 4 following a curved path. FIG. 3b shows a valve 2 having a single straight slit 4. In FIG. 3c, the slit arrangement 4 comprises two straight slits 4a and 4b which intersect one another to form a cross-shaped slit. In this case the two slits make an angle of approximately 90 degrees: this is preferred but not essential. FIG. 3d shows an example in which the slit arrangement 4 comprises three intersecting slits 4a, 4b and 4c which again are arranged to make substantially equal angles with one another: here the angle between two adjacent slits is around 60 degrees. The point of intersection is preferably at approximately the centre of the valve 2 but this is not essential.

In each case, the slit(s) are configured such that in its default position (when no stress is applied to the valve), the slit is substantially closed along its full length: that is, no open region of the membrane remains. This is desirable in order to ensure that the valve provides a full atmospheric seal. The fully closed membrane is substantially flat, or may lie in a (gently) curved plane in which case the convex side of the curve preferably faces the interior of the reagent bottle in use. When a probe or sleeve (described below) is pressed against the valve, the slit arrangement opens by undergoing a reversible deformation to permit passage of the component therethrough.

To achieve a tight seal, the valve 2 is preferably manufactured in two steps. First, the membrane is formed into the required shape, e.g. by injection moulding. Secondly, the one or more slits 4 are cut or sliced through the membrane using a sharp blade for example. In this way, there is no (or minimal) removal of the membrane material from the slit region. As such, in its closed configuration, the two cut edges of the slit meet one another exactly, forming a wholly closed seal.

The invention claimed is:

1. A dispensing apparatus for dispensing a reagent from a reagent bottle, the reagent bottle having a valve comprising a resilient membrane configured to extend across an opening in the reagent bottle, the resilient membrane having at least one slit extending therethrough the dispensing apparatus comprising:

a probe assembly having a probe adapted for insertion into the reagent bottle through the valve and an extraction mechanism for drawing reagent out of the reagent bottle through the probe, and a valve opening assembly adapted to open the valve of the reagent bottle such that the probe can pass through the valve without contacting the valve, wherein the valve opening assembly comprises a sleeve and an actuator for abutting the sleeve against the resilient membrane of the valve so as to deform the membrane and thereby open the at least one slit such that the probe can pass therethrough.

2. A dispensing apparatus according to claim 1 whereby the actuator is adapted to insert the sleeve through the at least one slit such that the sleeve isolates the valve from the sleeve interior through which the probe can pass.

3. A dispensing apparatus according to claim 1 wherein the sleeve comprises a hollow tube.

4. A dispensing apparatus according to claim 1 wherein the sleeve is formed of a metal or plastics material, a protectively coated metal or an inert polymer.

5. A dispensing apparatus according to claim 1 further comprising a washing mechanism for washing the sleeve.

6. A dispensing apparatus according to claim 1 wherein the sleeve diameter is sufficiently large relative to the valve such that only the outer surface of the membrane is contacted by the sleeve.

7. A dispensing apparatus according to claim 1 wherein the sleeve and actuator are configured such that the sleeve does not contact any reagent inside the reagent bottle.

8. A dispensing apparatus according claim 1 further comprising a probe drive mechanism for at least driving the probe into and out of the reagent bottle.

9. A dispensing apparatus according to claim 1 further comprising a controller for controlling the extraction mechanism and/or the valve opening assembly and/or the probe drive mechanism.

10. A dispensing apparatus according claim 1 adapted to accommodate a plurality of reagent bottles, each reagent bottle having a valve comprising a resilient membrane configured to extend across an opening in the reagent bottle, the resilient membrane having at least one slit extending therethrough, wherein the probe assembly is movable relative to the plurality of reagent bottles such that the probe can extract reagent from each or at least some of the plurality of reagent bottles.

11. A dispensing apparatus according to claim 10 wherein a valve opening assembly is provided for each reagent bottle.

12. A dispensing apparatus according to claim 10 wherein the valve opening assembly is moveable relative to the plurality of reagent bottles such that it can open the valves of each or at least some of the bottles.

13. A dispensing apparatus according to claim 1 further comprising one or more reagent bottles, each reagent bottle having a valve comprising a resilient membrane configured to extend across an opening in the reagent bottle, the resilient membrane having at least one slit extending therethrough.

14. An analyser for performing medical, chemical, proteomic and/or biochemical tests, comprising a dispensing apparatus for dispensing a reagent from a reagent bottle, the reagent bottle having a valve comprising a resilient membrane configured to extend across an opening in the reagent bottle, the resilient membrane having at least one slit extending therethrough, the dispensing apparatus comprising:

a probe assembly having a probe adapted for insertion into the reagent bottle through the valve and an extraction mechanism for drawing reagent out of the reagent bottle through the probe, and a valve opening assembly adapted to open the valve of the reagent bottle such that the probe can pass through the valve without contacting the valve, wherein the valve opening assembly comprises a sleeve and an actuator for abutting the sleeve against the resilient membrane of the valve so as to deform the membrane and thereby open the at least one slit such that the probe can pass therethrough.

* * * * *